United States Patent
Sekido

(10) Patent No.: US 10,925,464 B2
(45) Date of Patent: Feb. 23, 2021

(54) IMAGING UNIT AND ENDOSCOPE

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/778,027

(22) Filed: Jan. 31, 2020

(65) Prior Publication Data
US 2020/0163535 A1 May 28, 2020

Related U.S. Application Data

(63) Continuation of application No. PCT/JP2017/028322, filed on Aug. 3, 2017.

(51) Int. Cl.
*H05K 7/00* (2006.01)
*A61B 1/00* (2006.01)
(Continued)

(52) U.S. Cl.
CPC .......... *A61B 1/00114* (2013.01); *A61B 1/005* (2013.01); *A61B 1/05* (2013.01);
(Continued)

(58) Field of Classification Search
USPC ....................................................... 361/728
See application file for complete search history.

(56) References Cited

U.S. PATENT DOCUMENTS

2005/0056457 A1* 3/2005 Gall ..................... H05K 1/0281
174/254
2011/0245600 A1* 10/2011 Ishii ..................... H04N 5/2253
600/104
(Continued)

FOREIGN PATENT DOCUMENTS

JP 2010-263020 A 11/2010
JP 2013-098182 A 5/2013
(Continued)

OTHER PUBLICATIONS

International Search Report dated Oct. 3, 2017 issued in PCT/JP2017/028322.

*Primary Examiner* — Hung S. Bui
(74) *Attorney, Agent, or Firm* — Scully, Scott, Murphy & Presser, P.C.

(57) ABSTRACT

An imaging unit includes: an imaging element including a light receiver and a connection terminal formed on a back surface of the imaging element; a flexible printed circuit board including a connection electrode forming region, a cable connection electrode forming region, and a bent portion provided between the connection electrode forming region and the cable connection electrode forming region; and sealing resin filled around a junction between the imaging element and the flexible printed circuit board. The bent portion includes: a first bent portion that is bent toward the imaging element from the connection electrode forming region located parallelly to the light receiver of the imaging element; and a second bent portion that is provided continuously with the first bent portion and lets the cable connection electrode forming region extend in a direction opposite to a direction toward the imaging element.

10 Claims, 16 Drawing Sheets

(51) Int. Cl.
  *A61B 1/005*   (2006.01)
  *A61B 1/05*    (2006.01)
  *H01L 23/00*   (2006.01)
  *H04N 5/225*   (2006.01)
  *H05K 1/18*    (2006.01)
  *H05K 3/28*    (2006.01)
  *H05K 3/34*    (2006.01)

(52) U.S. Cl.
  CPC ............. *H01L 24/73* (2013.01); *H01L 24/92* (2013.01); *H04N 5/2251* (2013.01); *H05K 1/189* (2013.01); *H05K 3/28* (2013.01); *H05K 3/3436* (2013.01); *H01L 2224/73204* (2013.01); *H01L 2224/92125* (2013.01); *H04N 2005/2255* (2013.01); *H05K 2201/10121* (2013.01); *H05K 2201/10356* (2013.01); *H05K 2203/0195* (2013.01)

(56) References Cited

U.S. PATENT DOCUMENTS

2011/0249106 A1* 10/2011 Makino ................. H05K 1/189
                                                                    348/76
2015/0035960 A1*  2/2015 Nakamura ........... A61B 1/0011
                                                                    348/76
2018/0049627 A1   2/2018 Adachi et al.

FOREIGN PATENT DOCUMENTS

JP       2014-204275 A    10/2014
WO    WO 2016/203828 A1   12/2016

* cited by examiner

FIG.6
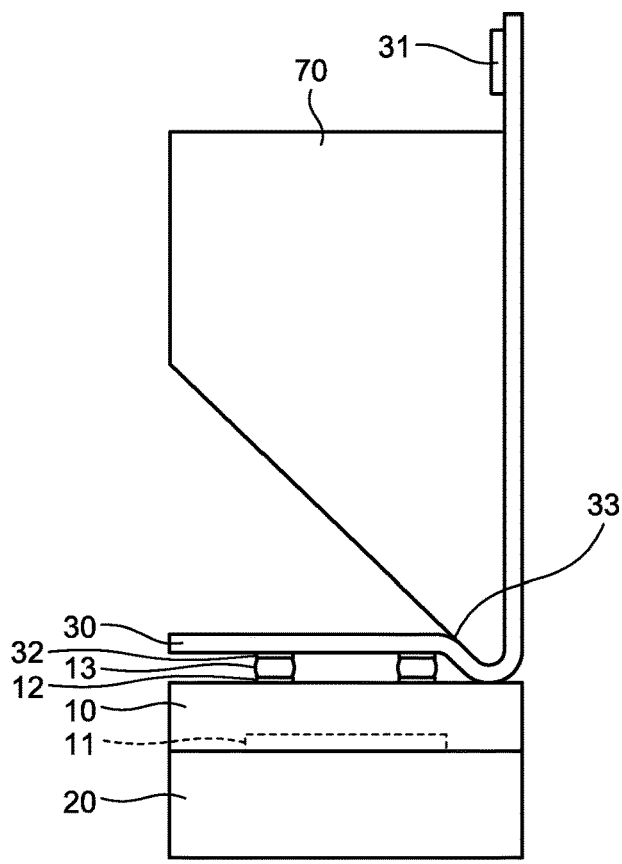
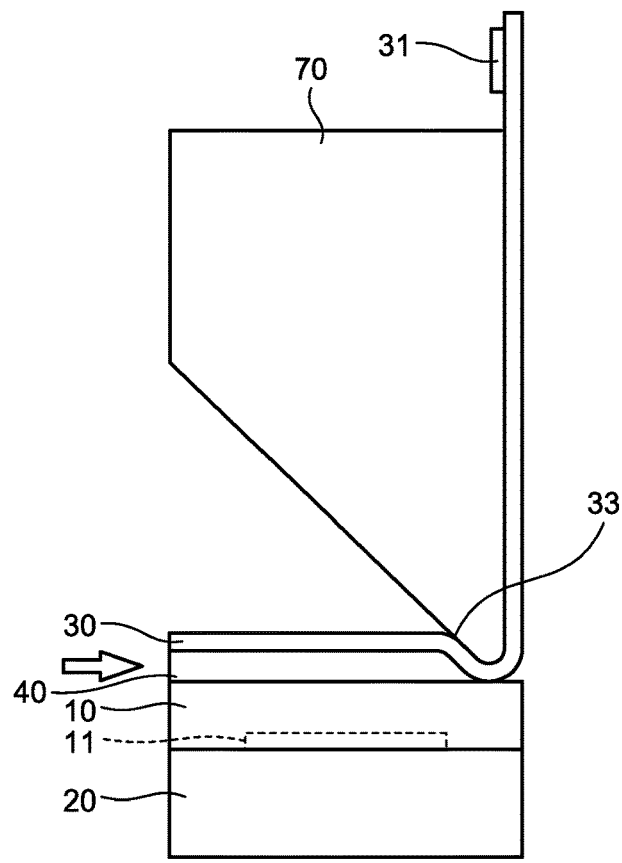

FIG.9
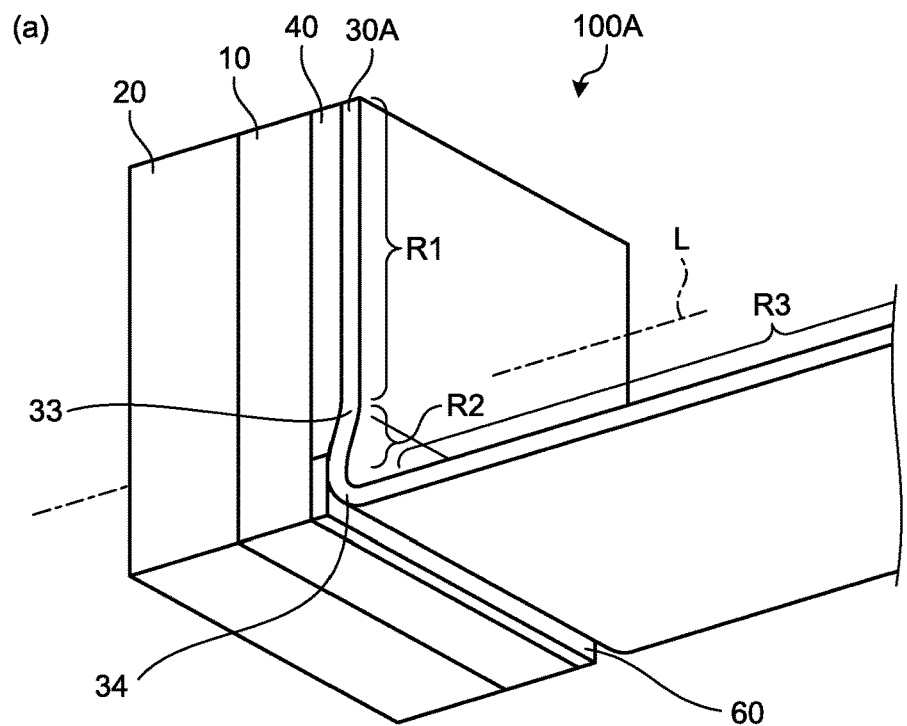
(a)
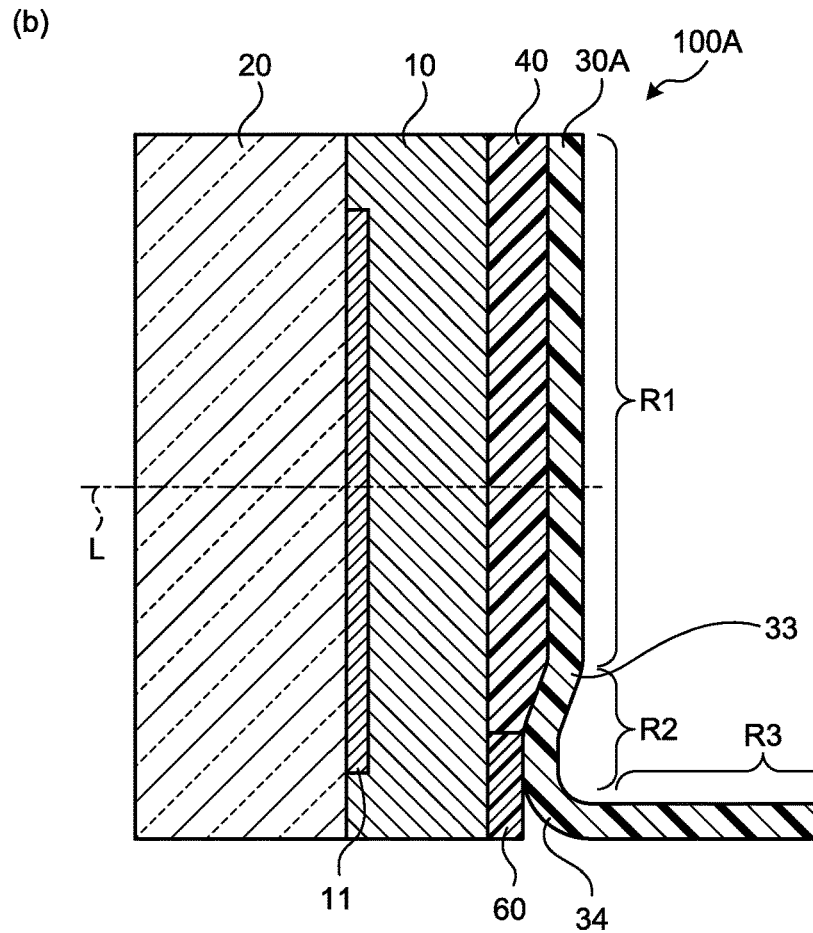
(b)

FIG.10
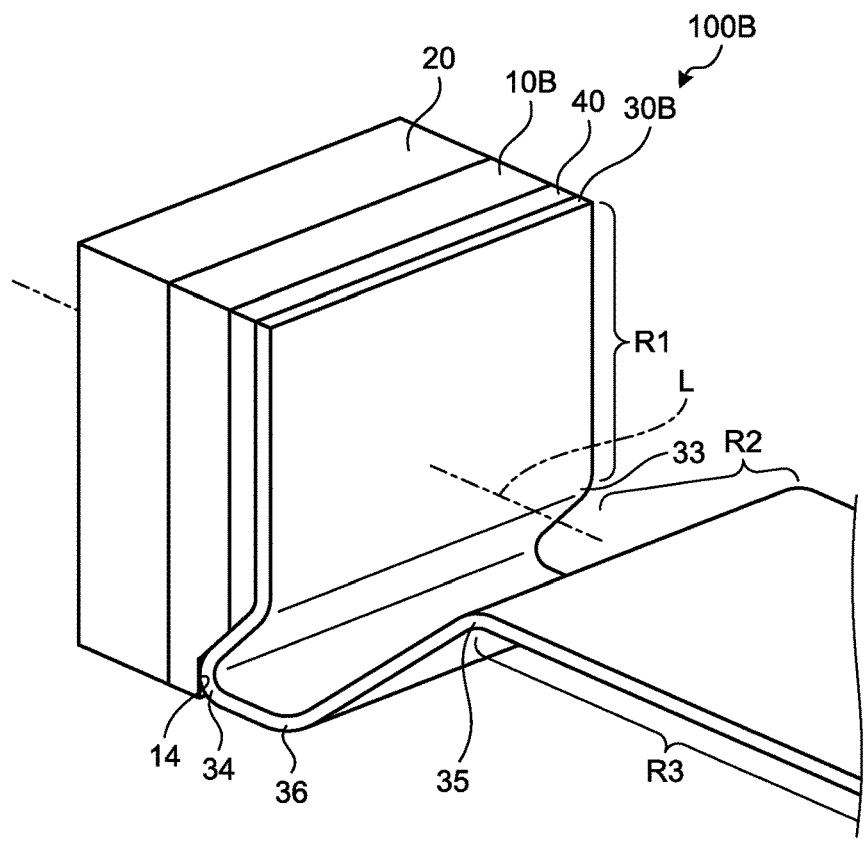
(a)
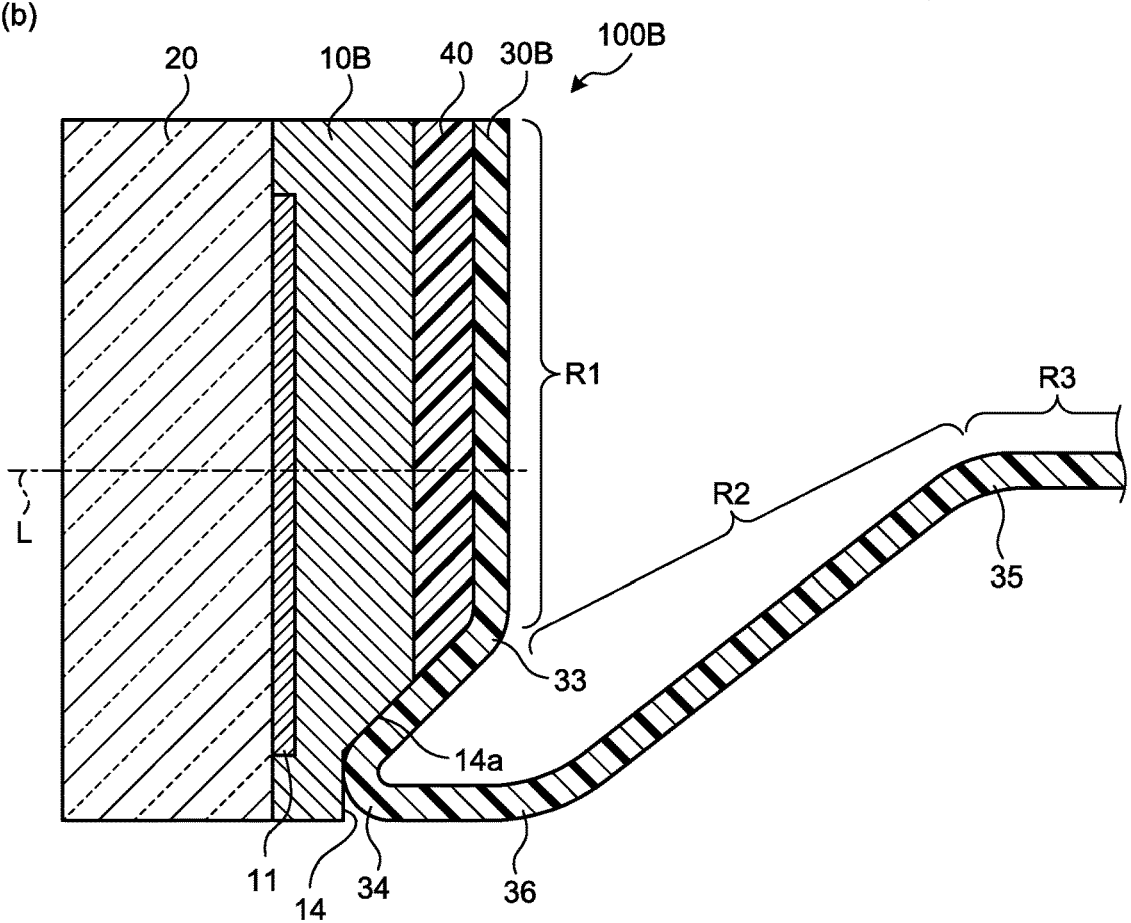
(b)

FIG.11
(a)
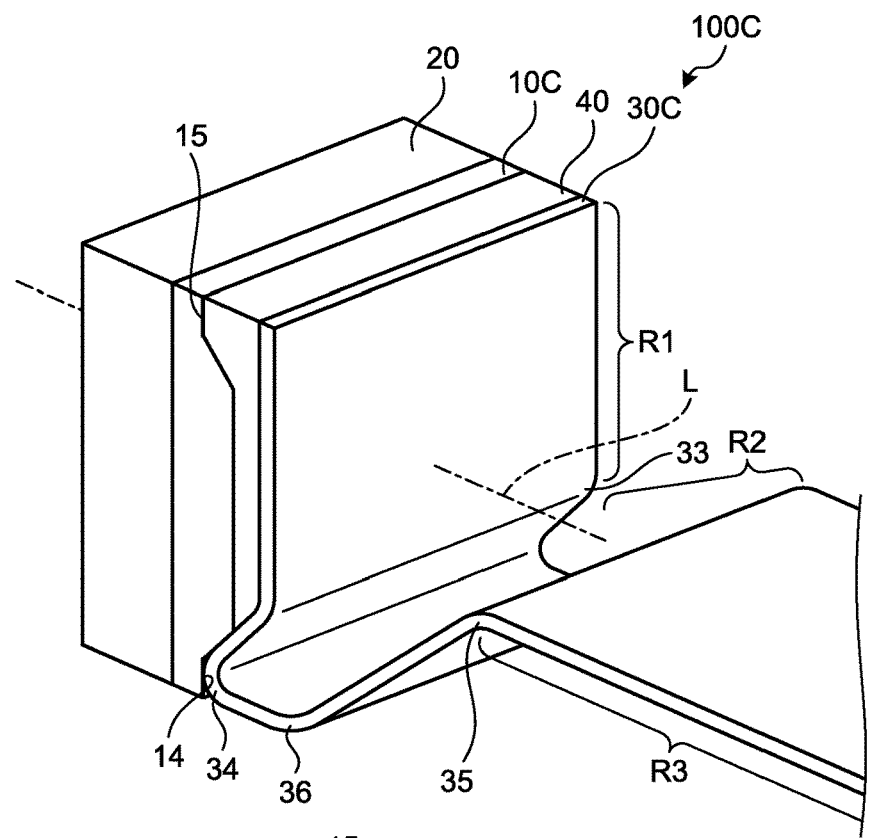
(b)
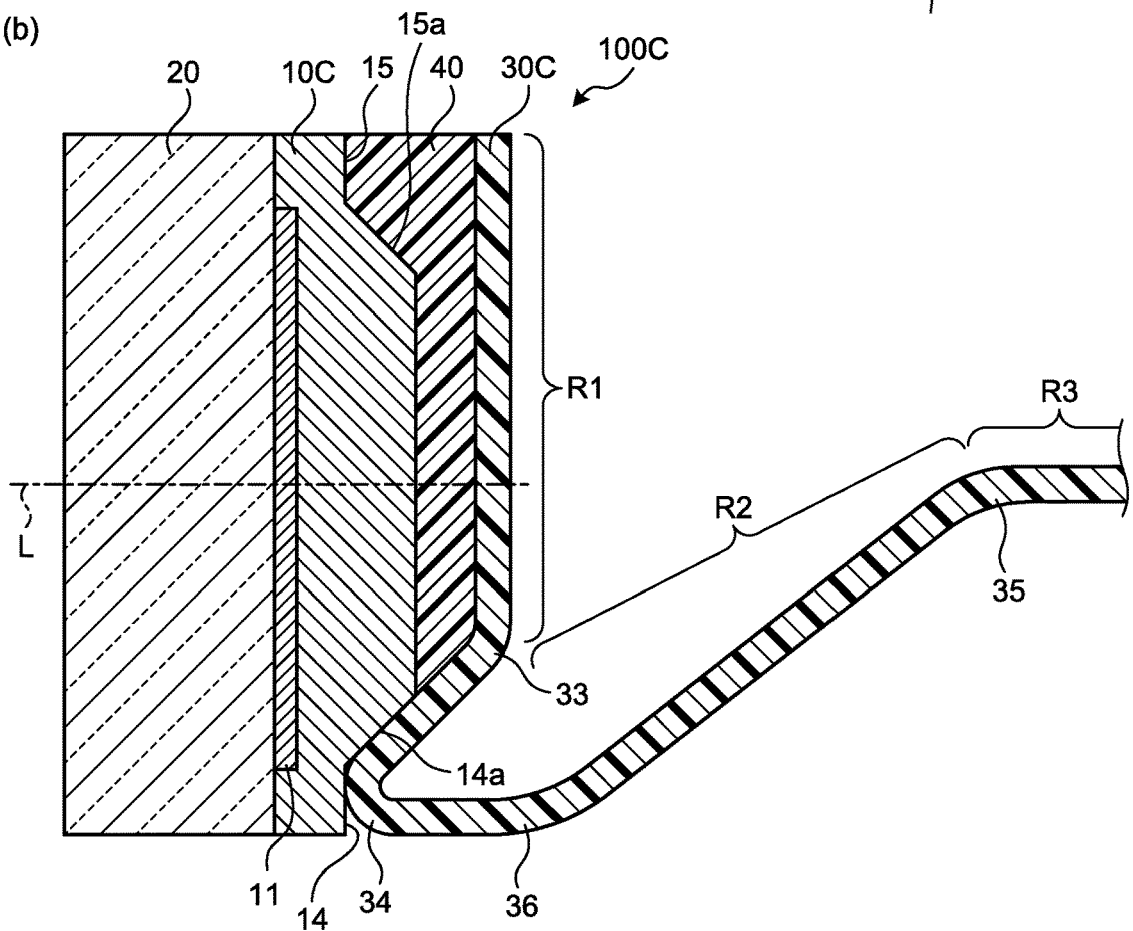

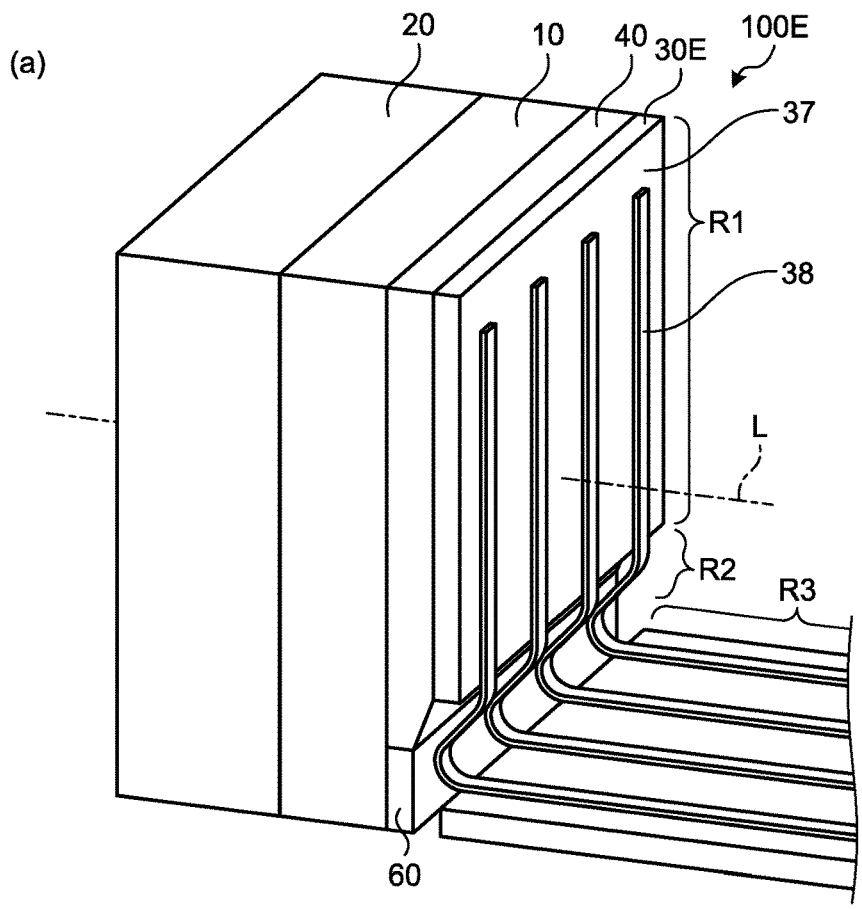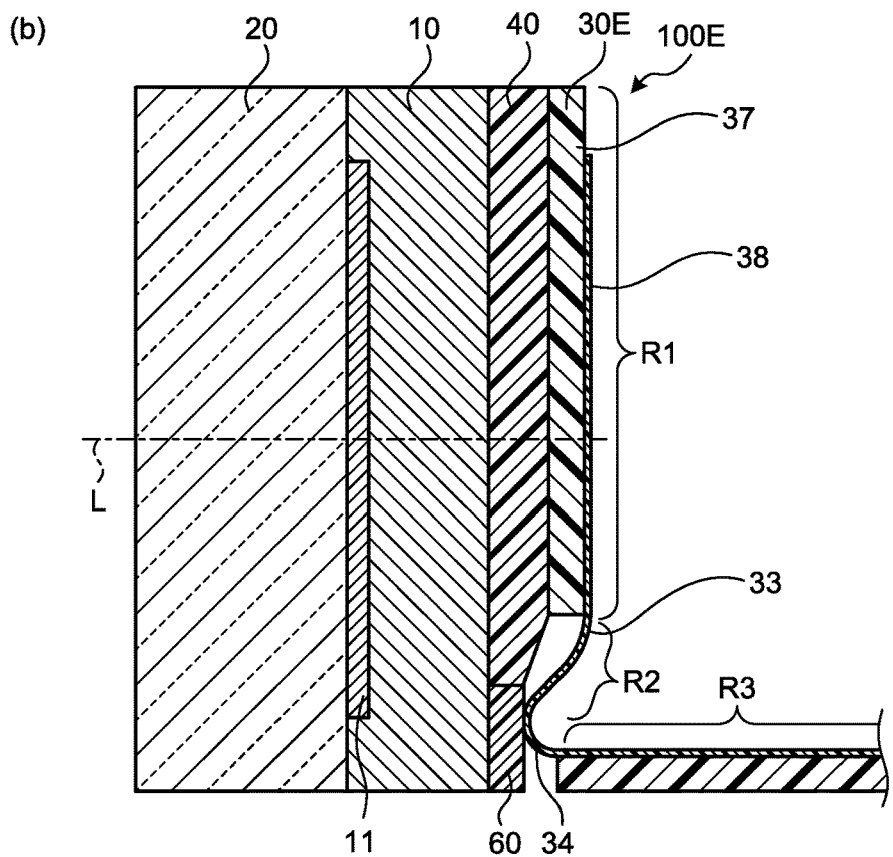
FIG.12

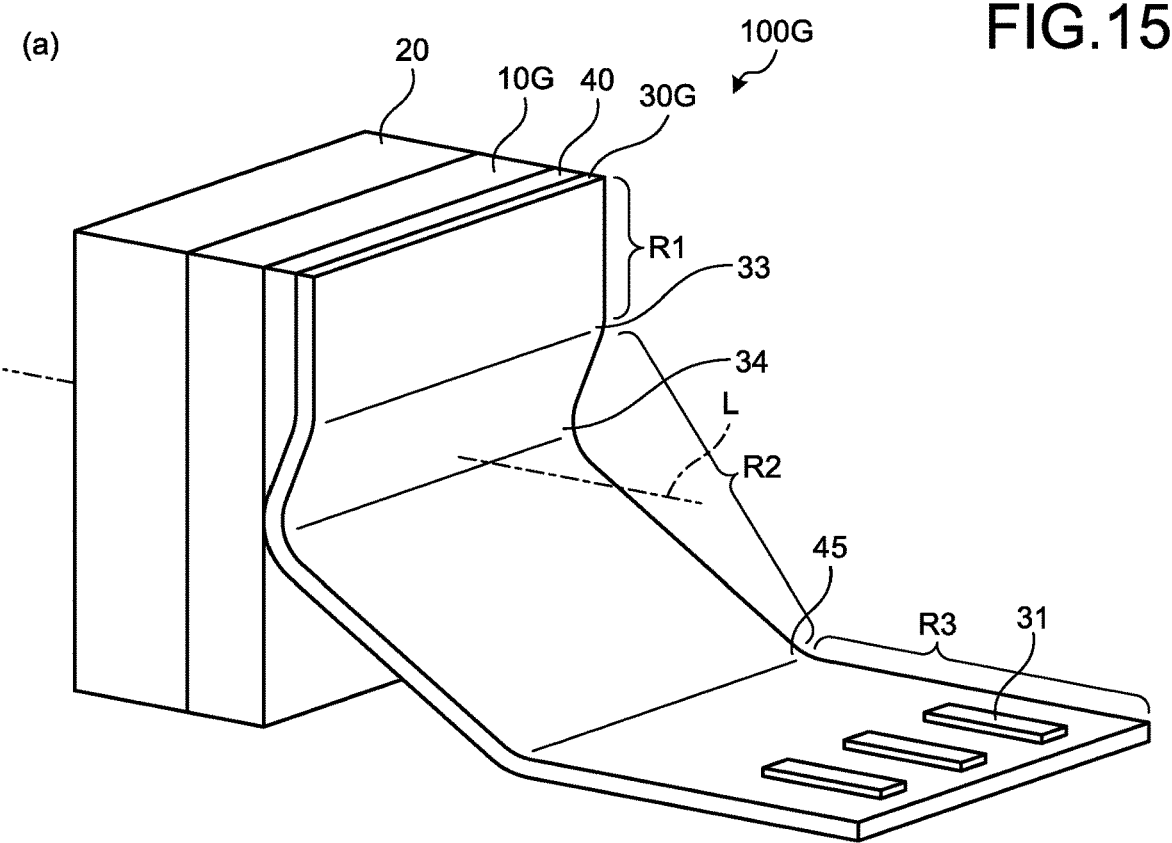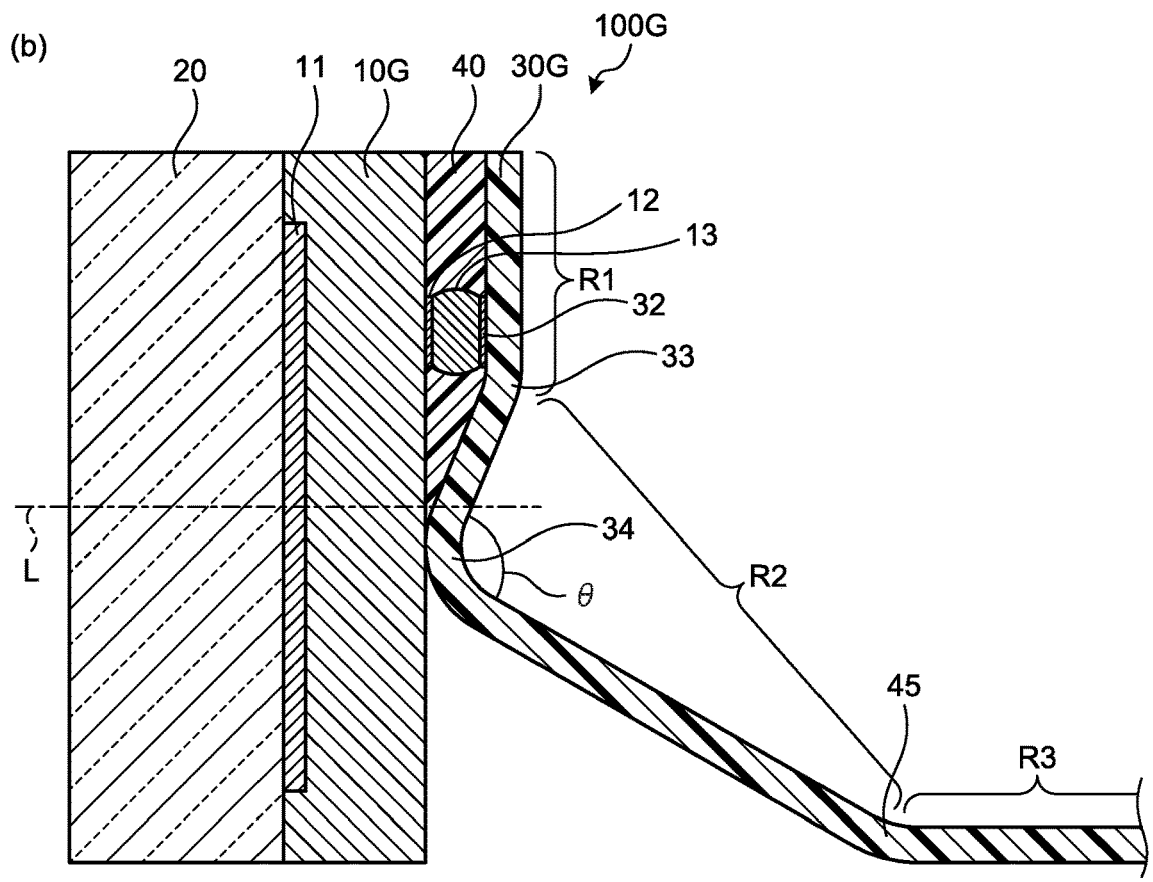
FIG.15

IMAGING UNIT AND ENDOSCOPE

CROSS-REFERENCE TO RELATED APPLICATION

This application is a continuation of International Application No. PCT/JP2017/028322, filed on Aug. 3, 2017, the entire contents of which are incorporated herein by reference.

BACKGROUND

1. Technical Field

The present disclosure relates to an imaging unit, and an endoscope having a distal end portion including the imaging unit.

2. Related Art

In the related art, endoscopes acquire in-vivo images of the interiors of subjects, such as patients, through insertion of their flexible insertion portions into the subjects, the flexible insertion portions having imaging units provided at distal ends thereof and being elongated. An imaging unit used in such an endoscope includes: an imaging element having a light receiving unit formed therein; and a flexible printed circuit board that is located adjacently to the imaging element on the back side of the imaging element and has electronic components, such as a condenser, a resistor, and an IC chip, mounted thereon (as seen in Japanese Laid-open Patent Publication No. 2010-263020).

SUMMARY

In some embodiments, an imaging unit includes: an imaging element including: a light receiver configured to receive light and generate an image signal by photoelectrically converting the light; and a connection terminal formed on a back surface of the imaging element; a flexible printed circuit board including: a connection electrode forming region where a connection electrode connected to the connection terminal is formed; a cable connection electrode forming region where a cable connection electrode connected to a cable is formed; and a bent portion provided between the connection electrode forming region and the cable connection electrode forming region; and sealing resin filled around a junction between the imaging element and the flexible printed circuit board. The bent portion includes: a first bent portion that is bent toward the imaging element from the connection electrode forming region located parallelly to the light receiver of the imaging element; and a second bent portion that is provided continuously with the first bent portion and lets the cable connection electrode forming region extend in a direction opposite to a direction toward the imaging element, and a part of the second bent portion is in contact with the back surface of the imaging element.

In some embodiments, an endoscope includes: the imaging unit; and an insertion portion that has a distal end portion and is insertable into a subject, the distal end portion being formed of a rigid member and being tubular. The insertion portion includes the imaging unit in a space inside the distal end portion.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a diagram for explanation of the manufacturing process of the imaging unit in FIG. 2;

FIG. 9 is a diagram schematically illustrating an imaging unit according to a second embodiment of the disclosure. (a) and (b) are a perspective view and a sectional view taken on a vertical plane including an optical axis, of the imaging unit, respectively;

FIG. 10 is a diagram schematically illustrating an imaging unit according to a third embodiment of the disclosure. (a) and (b) are a perspective view and a sectional view taken on a vertical plane including an optical axis, of the imaging unit, respectively;

FIG. 11 is a diagram schematically illustrating an imaging unit according to a modified example of the third embodiment of the disclosure. (a) and (b) are a perspective view and a sectional view taken on a vertical plane including an optical axis, of the imaging unit, respectively;

FIG. 12 is a diagram schematically illustrating an imaging unit according to a fourth embodiment of the disclosure. (a) and (b) are a perspective view and a sectional view taken on a vertical plane including an optical axis, of the imaging unit, respectively;

FIG. 15 is a diagram schematically illustrating an imaging unit according to a fifth embodiment of the disclosure. (a) and (b) are a perspective view and a sectional view taken on a vertical plane including an optical axis, of an imaging unit, respectively.

DETAILED DESCRIPTION

Described hereinafter as modes for implementation of the disclosure (hereinafter, referred to as "embodiments") are endoscope systems each including an imaging unit. The disclosure is not limited by these embodiments.

Furthermore, each drawing referred to in the following description schematically illustrates shapes, sizes, and positional relations, merely to an extent that allows contents of the disclosure to be understood. That is, the disclosure is not limited only to the shapes, sizes, and positional relations, exemplified by the drawings. In addition, the drawings may include a portion that differs in its dimensions and proportions among the drawings.

First Embodiment

Figure 1:
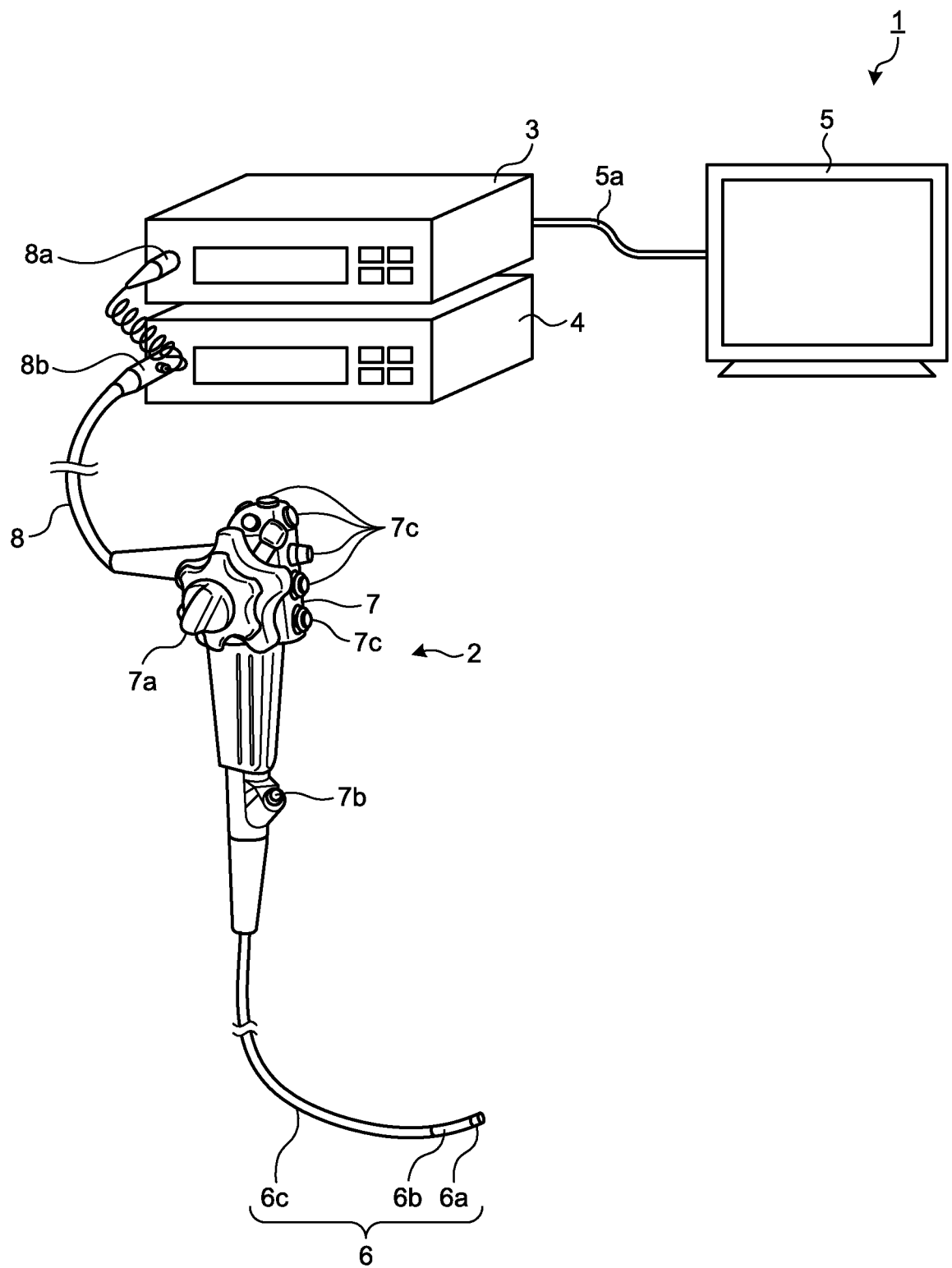
FIG. 1 is a diagram schematically illustrating an overall configuration of an endoscope system according to a first embodiment of the disclosure.

FIG. 1 is a diagram schematically illustrating an overall configuration of an endoscope system 1 according to a first embodiment of the disclosure. As illustrated in FIG. 1, the endoscope system 1 according to the first embodiment includes an endoscope 2 that is introduced into a subject and generates an image signal by capturing an image of the interior of the body of the subject; an information processing device 3 that performs predetermined image processing on the image signal captured by the endoscope 2 and controls each device in the endoscope system 1; a light source device 4 that generates illumination light for the endoscope 2; and a display device 5 that displays an image for the image signal that has been image-processed by the information processing device 3.

The endoscope 2 includes: an insertion portion 6 that is inserted into the subject; an operating unit 7 that is on a proximal end side of the insertion portion 6 and held by an operator; and a universal cord 8 that extends from the operating unit 7 and is flexible.

The insertion portion 6 is realized by use of an illumination fiber (a light guide cable), an electric cable, and an optical fiber. The insertion portion 6 includes: a distal end portion 6a having a later described imaging unit built therein; a bending portion 6b that is formed of plural bending pieces and is freely bendable; and a flexible tube portion 6c that is provided on a proximal end side of the bending portion 6b and has flexibility. The distal end portion 6a is provided with: an illumination unit that illuminates the interior of the subject via an illumination lens; an observation unit that captures an image of the interior of the subject; an opening section that provides communication with a surgical tool channel; and an air and water feeding nozzle (not illustrated in the drawings).

The operating unit 7 includes: a bending knob 7a that causes the bending portion 6b to bend upward and downward, and leftward and rightward; a surgical tool insertion portion 7b through which a surgical tool, such as biological forceps or a laser scalpel, is inserted into a body cavity of the subject; and plural switches for operation of peripheral devices, such as an air feeding device, a water feeding device, and a gas feeding device. The surgical tool inserted from the surgical tool insertion portion 7b comes out from the opening section at a distal end of the insertion portion 6 via the surgical tool channel provided inside the insertion portion 6.

The universal cord 8 is formed by use of an illumination fiber and a cable. The universal cord 8 is branched into end portions at a proximal end thereof, and one of the branched end portions is a connector 8a and the other branched end portion is a connector 8b. The connector 8a is freely attachable to and detachable from a connector of the information processing device 3. The connector 8b is freely attachable to and detachable from the light source device 4. The universal cord 8 transmits illumination light emitted from the light source device 4, to the distal end portion 6a, via the connector 8b and the illumination fiber. Furthermore, the universal cord 8 transmits an image signal captured by the later described imaging unit, to the information processing device 3, via the cable and the connector 8a.

The information processing device 3 executes the predetermined image processing on the image signal output from the connector 8a and controls the overall endoscope system 1.

The light source device 4 is formed by use of: a light source that emits light; and a condenser lens. Under control of the information processing device 3, the light source device 4 emits light from the light source and supplies the light as illumination light for the interior of the subject that is a subject to be imaged, to the endoscope 2 connected to the light source device 4 via the connector 8b and the illumination fiber of the universal cord 8.

The display device 5 is formed by use a display having liquid crystal or organic electroluminescence (EL) used therein. The display device 5 displays, via a video cable 5a, various types of information including the image that has been subjected to the predetermined image processing by the information processing device 3. As a result, the operator is able to perform observation and determination of characteristics, of a desired position in the subject by operating the endoscope 2 while looking at the image (in-vivo image) displayed by the display device 5.

Figure 2:
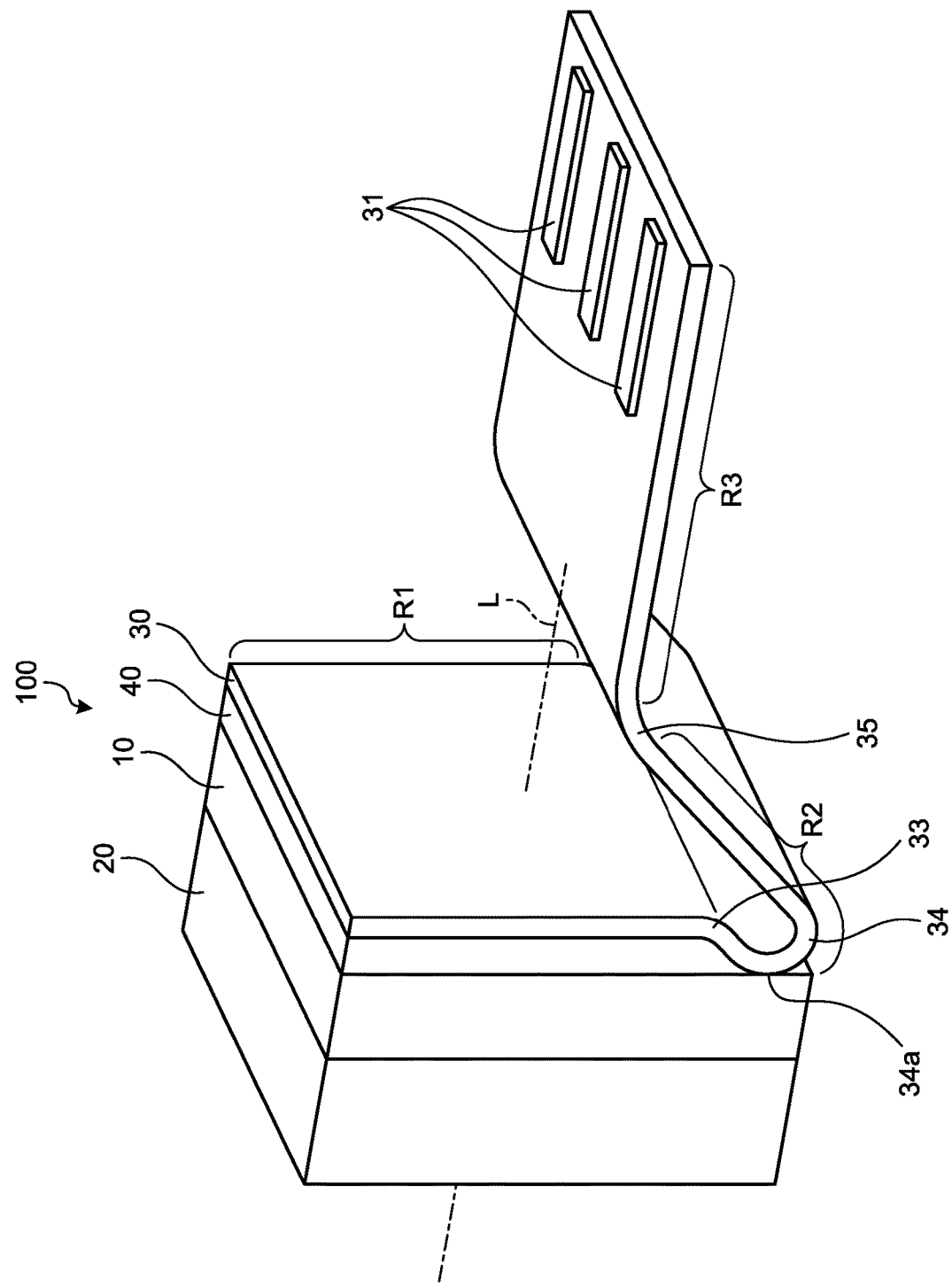
FIG. 2 is a perspective view of an imaging unit used in an endoscope system according to the first embodiment of the disclosure.
Figure 3:
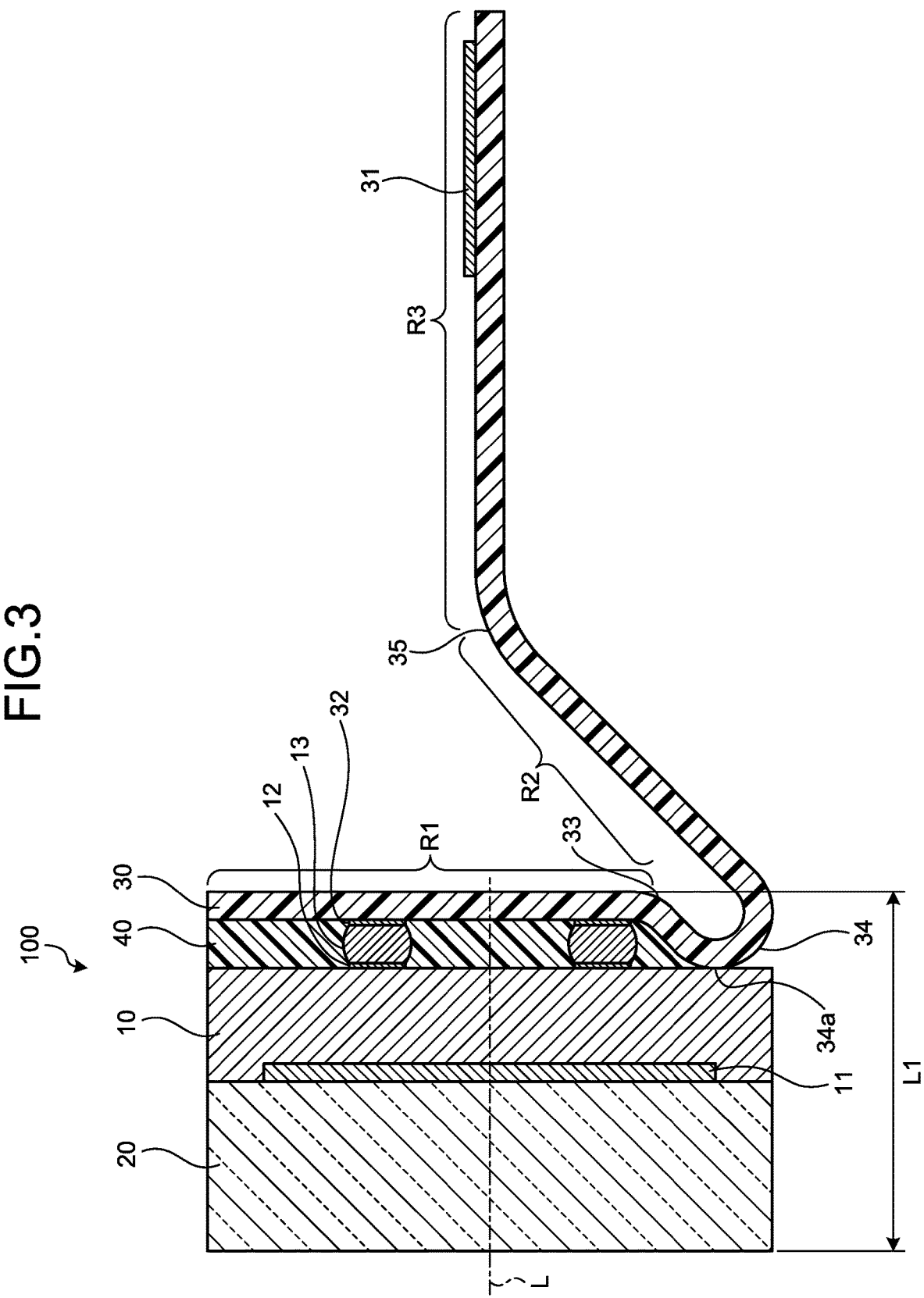
FIG. 3 is a sectional view taken on a vertical plane including an optical axis of the imaging unit in FIG. 2.

Described next in detail is an imaging unit 100 used in the endoscope system 1. FIG. 2 is a perspective view of the imaging unit 100 used in the endoscope system 1 according to the first embodiment of the disclosure. FIG. 3 is a sectional view taken on a vertical plane including an optical axis of the imaging unit 100 in FIG. 2. In FIG. 2 and FIG. 3, illustration of cables 50 has been omitted.

The imaging unit 100 includes: an imaging element 10 having a light receiving unit 11 that generates an image signal by receiving light and photoelectrically converting the light, the imaging element 10 having connection terminals 12 formed on a back surface of the imaging element 10; a cover glass 20 that protects the light receiving unit 11 of the imaging element 10; a flexible printed circuit board 30 (hereinafter, referred to as the "FPC board") having a connection electrode forming region R1 where connection electrodes 32 connected to the connection terminals 12 are formed, a bent portion R2, a cable connection electrode forming region R3 where cable connection electrodes 31 connected to cables are formed; and sealing resin 40 that is filled around a junction between the imaging element 10 and the FPC board 30.

The light receiving unit 11, such as a CMOS element, is formed on a front surface side of the imaging element 10. The light receiving unit 11 is connected to the connection terminals 12 on a back surface side of the imaging element 10, via through-connections, which are formed of through-silicon vias (TSVs) and not illustrated in the drawings. Bumps 13 formed of solder are formed on the connection terminals 12.

The bent portion R2 of the FPC board 30 is formed of: a first bent portion 33 that bends toward the imaging element 10 from the connection electrode forming region R1 located parallelly to the light receiving unit 11 of the imaging element 10; a second bent portion 34 that lets the cable connection electrode forming region R3 extend in a direction opposite to a direction toward the imaging element 10; and a third bent portion 35 that is bent such that the cable connection electrode forming region R3 is positioned near the center of a plane of projection of the imaging element 10, the projection being made in an optical axis L direction of the imaging element 10. The first bent portion 33, the second bent portion 34, and the third bent portion 35 are bent such that the FPC board 30 is positioned in the plane of projection of the imaging element 10, the projection being made in the optical axis L direction. Furthermore, the second bent portion 34 is in contact with the back surface of the imaging element 10 at an end portion 34a thereof toward the imaging element 10. The end portion 34a of the second bent portion 34 is in line contact or surface contact with the imaging element 10 over the entire width (in a depth direction of the page) of the imaging element 10.

Figure 4:
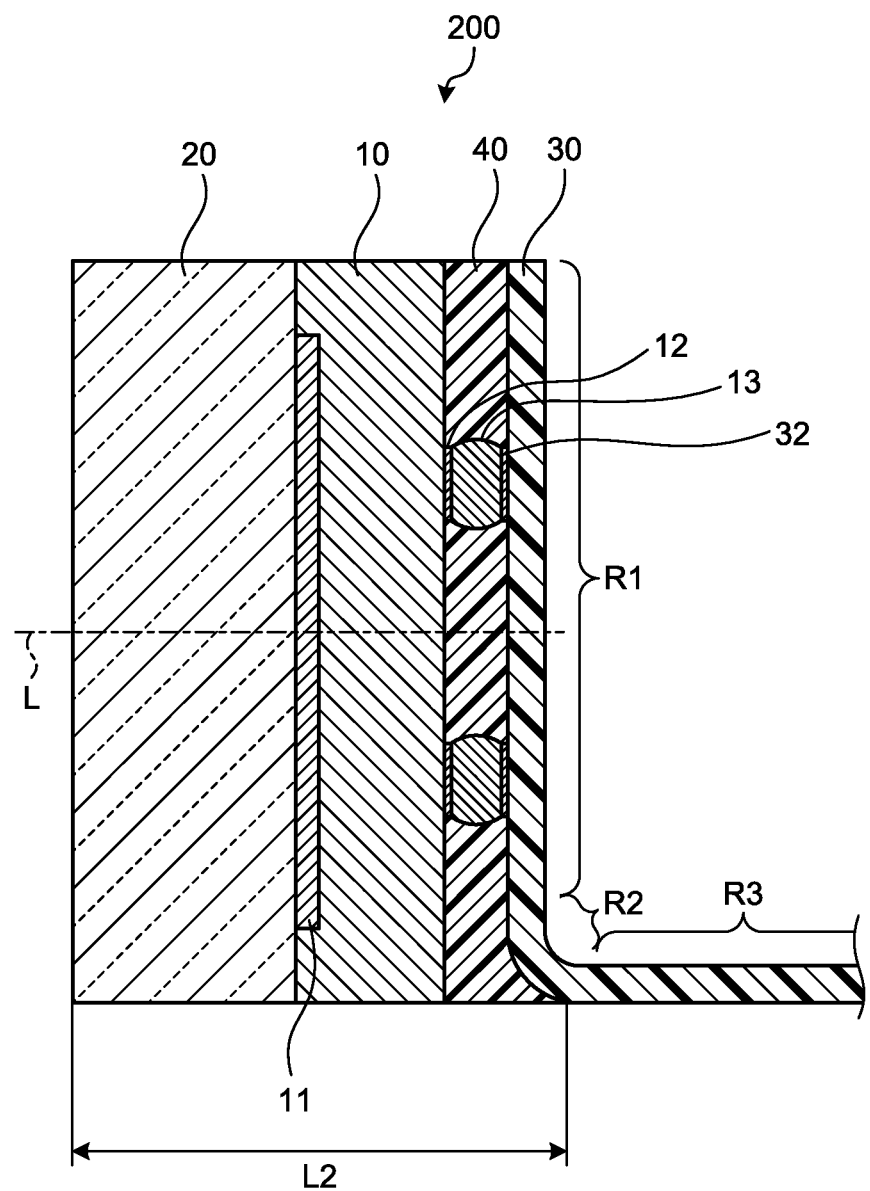
FIG. 4 is a sectional view taken on a vertical plane including an optical axis of a conventional imaging unit.

FIG. 4 is a sectional view taken on a vertical plane including an optical axis of a conventional imaging unit 200. Connection electrodes 32 formed in a connection electrode forming region R1 of an FPC board 30 are connected to connection terminals 12 of an imaging element 10 and the FPC board 30 is bent at a bent portion R2 for connection of cables to the FPC board 30 in a cable connection electrode forming region R3 that is not illustrated entirely, but because sealing resin 40 creeps up the bent portion R2, length L2 of a rigid portion of the imaging unit 200 is long.

According to the first embodiment, because the first bent portion 33 is bent toward the imaging element 10 and the end portion 34a of the second bent portion 34 is in contact with the imaging element 10, the sealing resin 40 filled around the junction between the imaging element 10 and the FPC board 30 is blocked at a contacting portion where the end portion 34a is in contact with the imaging element 10 and does not flow outside the end portion 34a (rightward from the center of the bend of the second bent portion 34 in FIG. 3). As a result, the sealing resin 40 is prevented from creeping up the bent portion R2 and length L1 of a rigid portion of the imaging unit 100 is able to be controlled.

Furthermore, according to the first embodiment, by provision of the third bent portion 35, the cable connection electrode forming region R3 is positioned near the center of the plane of projection of the imaging element 10, the projection being made in the optical axis L direction. By the cable connection electrode forming region R3 being positioned near the center of the plane of projection of the imaging element 10, the projection being made in the optical axis L direction, space is able to be utilized effectively at the distal end portion 6a of the endoscope 2.

Figure 5:
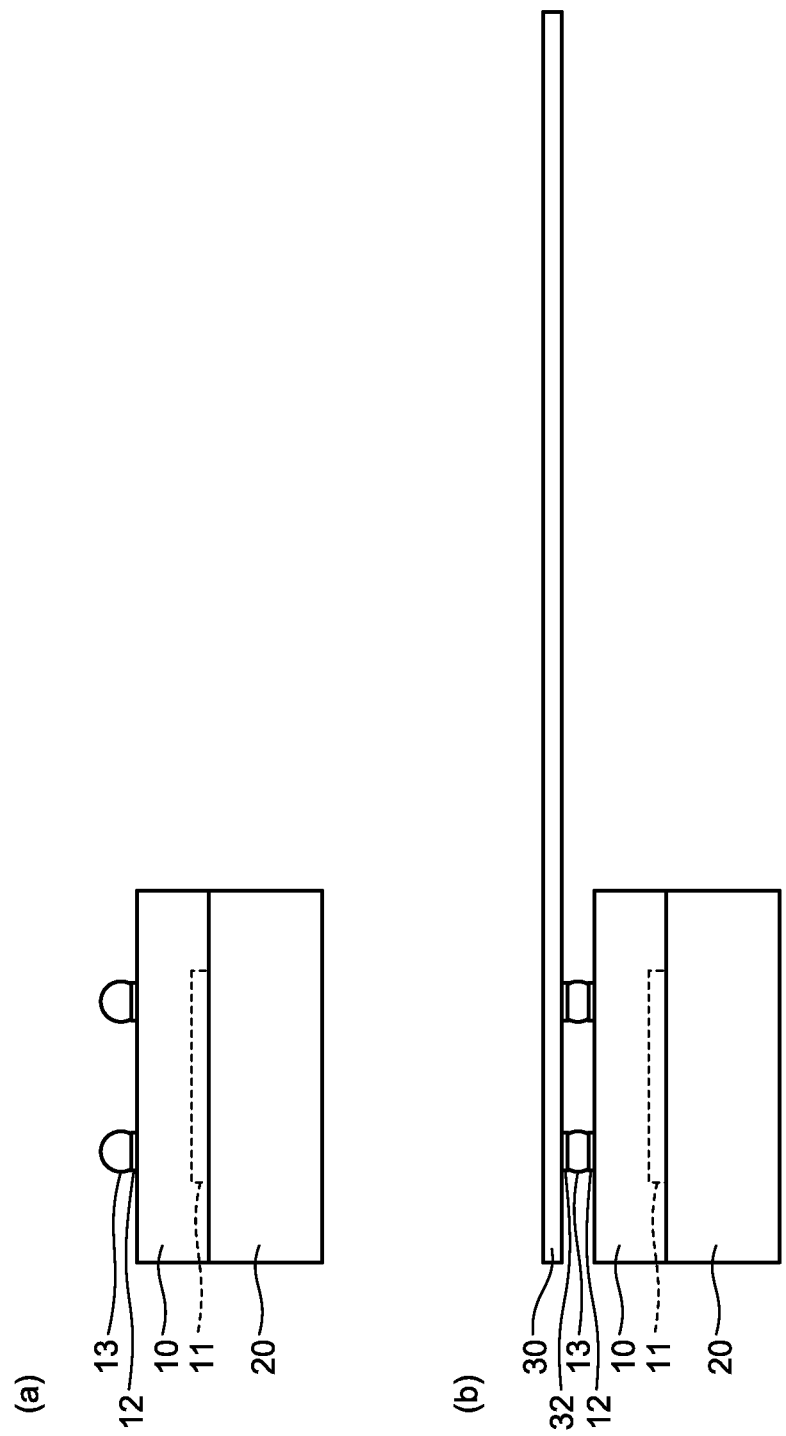
FIG. 5 is a diagram for explanation of a manufacturing process of the imaging unit in FIG. 2.
Figure 7:
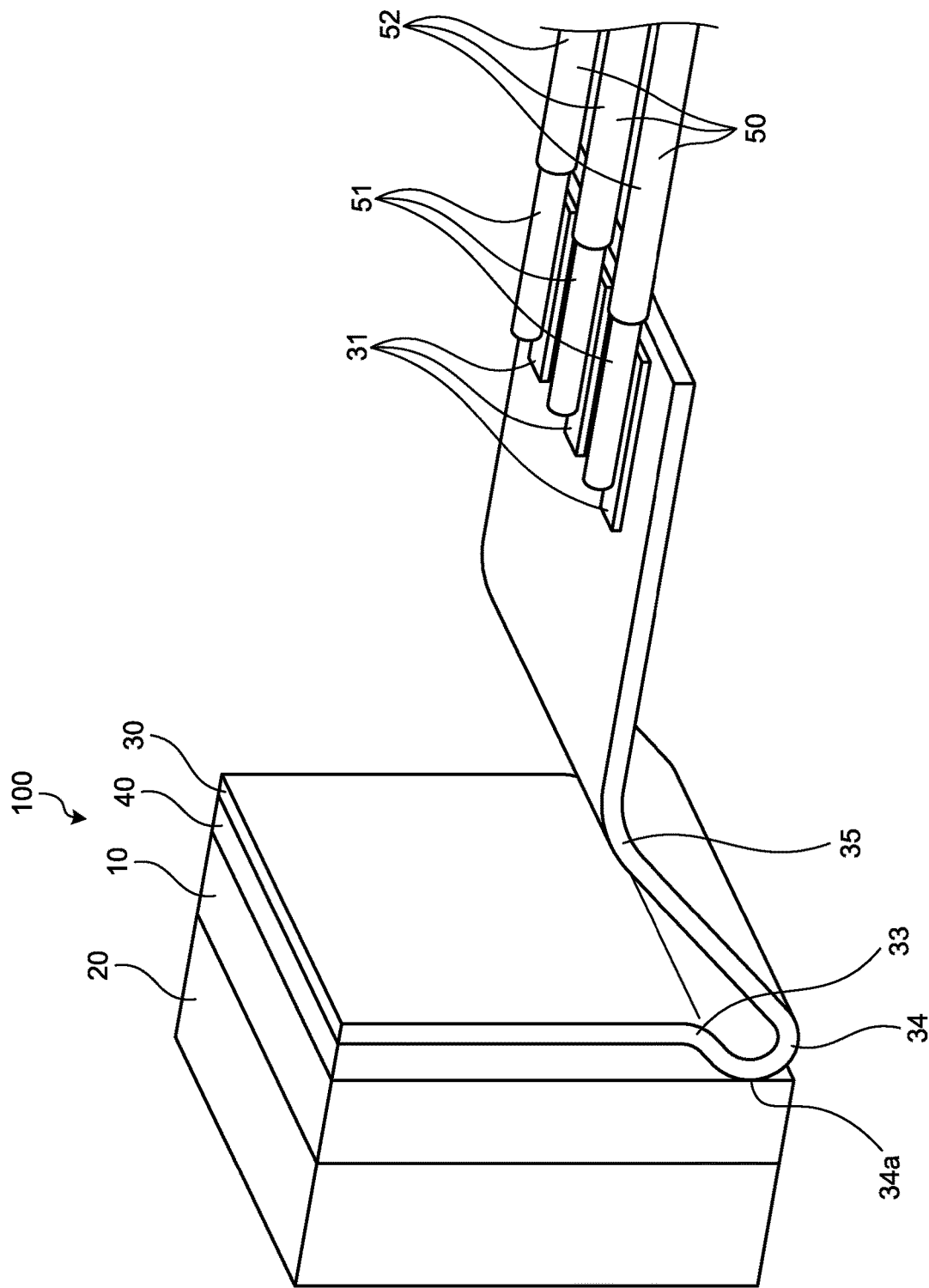
FIG. 7 is a diagram for explanation of the manufacturing process of the imaging unit in FIG. 2.

Described next by reference to FIG. 5 to FIG. 7 is a manufacturing process of the imaging unit 100. FIG. 5 to FIG. 7 are diagrams for explanation of the manufacturing process of the imaging unit 100 in FIG. 2.

First of all, as illustrated in (a) of FIG. 5, the bumps 13 are formed on the connection terminals 12 on the back surface of the imaging element 10, and as illustrated in (b) of FIG. 5, the bumps 13 are connected to the connection electrodes 32 on the FPC board 30 by reflow.

After this connection, as illustrated in (a) of FIG. 6, the first bent portion 33 is formed by the FPC board 30 being bent toward the imaging element 10 through use of a board bending tool 70, and the FPC board 30 is thereby brought into contact with the back surface of the imaging element 10.

In the state where the FPC board 30 has been brought into contact with the back surface of the imaging element 10 by the board bending tool 70, the sealing resin 40 is filled to the junction between the imaging element 10 and the FPC board 30 from a direction indicated by an arrow in (b) of FIG. 6 and thermally cured. The sealing resin 40 is filled to the junction between the imaging element 10 and the FPC board 30 through the capillary phenomenon, but since the FPC board 30 has been pressed toward the imaging element 10 by the board bending tool 70, the sealing resin 40 is prevented from flowing out in a direction opposite to the direction from which the sealing resin 40 is filled.

After the sealing resin 40 has been cured, the second bent portion 34 and the third bent portion 35 are formed by bending of the FPC board by use of a board bending tool not illustrated in the drawings, and as illustrated in FIG. 7, the cables 50 having their coverings 52 removed at distal end portions of the cables 50 and having their core wires 51 exposed are connected to the cable connection electrodes 31 by an electrically conductive member not illustrated in the drawings.

Figure 8:
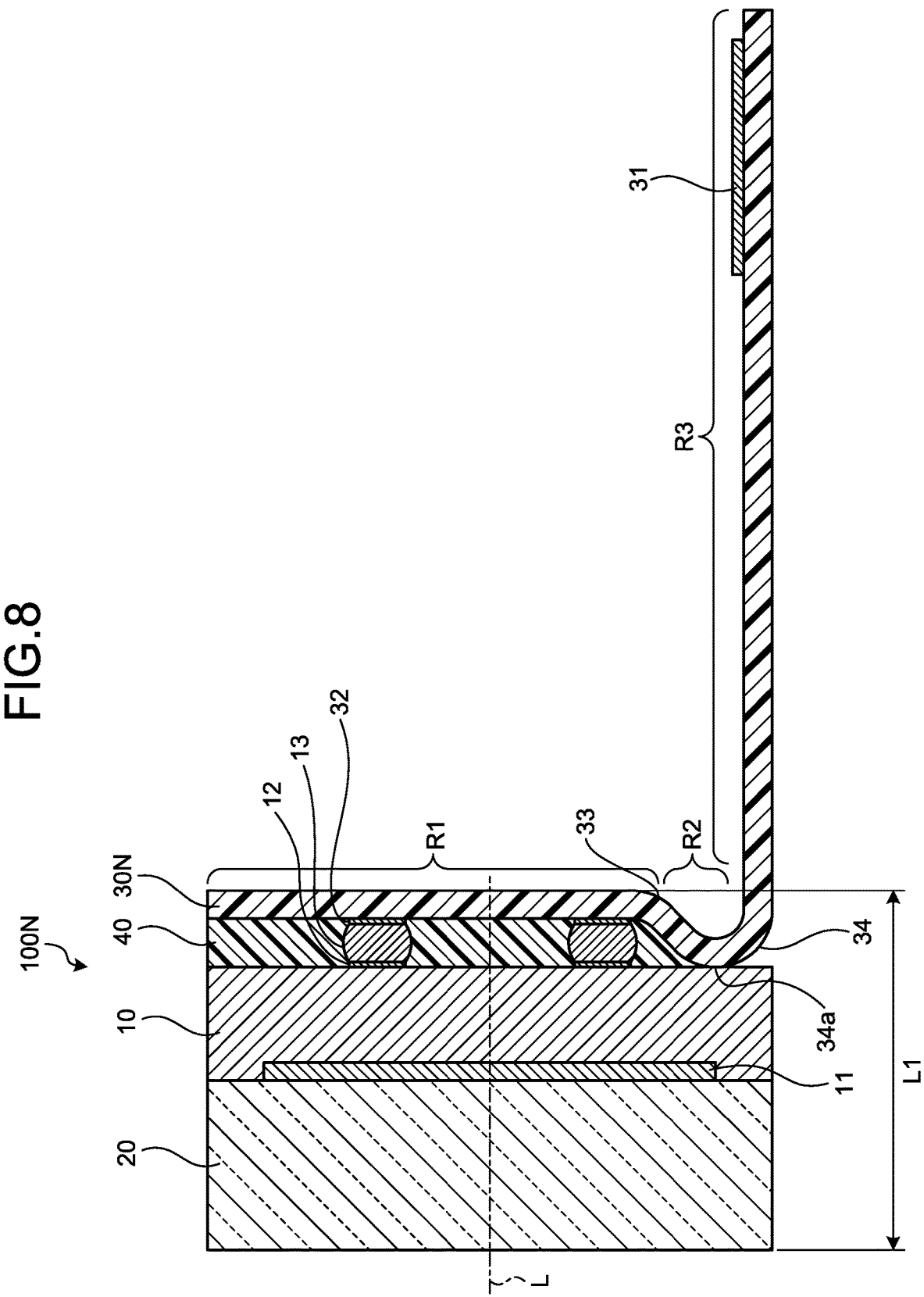
FIG. 8 is a sectional view taken on a vertical plane including an optical axis of an imaging unit according to a modified example of the first embodiment of the disclosure.

As described above, the imaging unit 100 short in the length L1 of the rigid portion is able to be manufactured. According to the above description, the bumps 13 are formed on the connection terminals 12 of the imaging element 10, but the bumps 13 may be formed on the connection electrodes 32 on the FPC board 30 instead. Furthermore, according to the first embodiment, the third bent portion 35 is formed in the FPC board 30, but as long as the FPC board 30 is positioned in the plane of projection of the imaging element 10, the projection being made in the optical axis L direction, the bent portion R2 may be formed of just the first bent portion 33 and second bent portion 34. FIG. 8 is a sectional view taken on a vertical plane including an optical axis of an imaging unit 100N according to a modified example of the first embodiment of the disclosure. In the imaging unit 100N, a bent portion R2 of an FPC board 30N is formed of: a first bent portion 33 that is bent toward an imaging element 10 from a connection electrode forming region R1 located parallelly to a light receiving unit 11 of the imaging element 10; and a second bent portion 34 that lets a cable connection electrode forming region R3 extend in a direction opposite to a direction toward the imaging element 10. The first bent portion 33 and the second bent portion 34 are bent such that the FPC board 30N is positioned in a plane of projection of the imaging element 10, the projection being made in an optical axis L direction of the imaging element 10. The second bent portion 34 is in line contact with the imaging element 10 over the entire width (in a depth direction of the page) of the imaging element 10. In the imaging unit 100N also, because sealing resin 40 filled around the junction between the imaging element 10 and the FPC board 30N is blocked at the contacting portion and prevented from flowing outside an end portion 34a (toward the center of the bend of the second bent portion 34); the sealing resin 40 is prevented from creeping up the bent portion R2 and length L1 of a rigid portion of the imaging unit 100N is able to be controlled.

Second Embodiment

According to a second embodiment of the disclosure, a protruding portion 60 is formed at a position of a back surface of an imaging element 10, the position being where a bent portion R2 is positioned. FIG. 9 is a diagram schematically illustrating an imaging unit 100A according to a second embodiment of the disclosure. (a) of FIG. 9 and (b) of FIG. 9 are a perspective view and a sectional view taken on a vertical plane including an optical axis, of an imaging unit 100A, respectively.

In the imaging unit 100A, the protruding portion 60 is formed at the position of the back surface of the imaging element 10, the position being where the bent portion R2 of an FPC board 30A is positioned. The protruding portion 60 is formed of a material, such as resin, metal, glass, or ceramic, and is formed on the imaging element 10 over the entire width (in a depth direction of the page) of the imaging element 10. According to this specification, the protruding portion 60 is also included in the back surface of the imaging element 10.

The bent portion R2 of the FPC board 30A is formed of: a first bent portion 33 that is bent toward the imaging element 10 from a connection electrode forming region R1 located parallelly to a light receiving unit 11 of the imaging element 10; and a second bent portion 34 that lets a cable connection electrode forming region R3 extend in a direction opposite to a direction toward the imaging element 10. The first bent portion 33 and the second bent portion 34 are bent such that the FPC board 30A is positioned in a plane of projection of the imaging element 10, the projection being made in an optical axis L direction of the imaging element 10. The second bent portion 34 is in line contact or surface contact with the protruding portion 60 over the entire width (in a depth direction of the page) of the protruding portion 60.

According to the second embodiment, because the protruding portion 60 is provided on the back surface of the imaging element 10 and the second bent portion 34 is in contact with the protruding portion 60; outflow of sealing resin 40 is prevented and length of a rigid portion is thus controlled, and the bending radii R are able to be increased such that the first bent portion 33 and second bent portion 34 of the FPC board 30A are gently curved and bending stress exerted on the FPC board 30A is thus able to be reduced.

According to the second embodiment, the bent portion R2 is formed of the first bent portion 33 and the second bent portion 34, but as long as the FPC board 30A is positioned in the plane of projection of the imaging element 10, the projection being made in the optical axis L direction, the cable connection electrode forming region R3 of the FPC board 30A may be positioned near the center of the plane of projection of the imaging element 10, the projection being made in the optical axis L direction, by formation of a third bent portion 35.

Third Embodiment

According to a third embodiment of the disclosure, a notched portion 14 having a wall 14a forming an inclined surface is formed at a position of a back surface of an imaging element 10B, the position being where a bent portion R2 is positioned. FIG. 10 is a diagram schematically illustrating an imaging unit 100B according to a third embodiment of the disclosure. (a) of FIG. 10 and (b) of FIG. 10 are a perspective view and a sectional view taken on a vertical plane including an optical axis, of an imaging unit 100B, respectively.

In the imaging unit 100B, the notched portion 14 having the wall 14a forming the inclined surface is formed at the position of the back surface of the imaging element 10B, the position being where the bent portion R2 of an FPC board 30B is positioned. The notched portion 14 is formed over the entire width (in a depth direction of the page) of the imaging element 10B.

The bent portion R2 of the FPC board 30B is formed of: a first bent portion 33 that is bent toward the imaging element 10B from a connection electrode forming region R1 located parallelly to a light receiving unit 11 of the imaging element 10B; a second bent portion 34 that lets a cable connection electrode forming region R3 extend in a direction opposite to a direction toward the imaging element 10B; a third bent portion 35 that is bent such that the cable connection electrode forming region R3 is positioned near the center of a plane of projection of the imaging element 10B, the projection being made in an optical axis L direction of the imaging element 10B; and a fourth bent portion 36 that is positioned between the second bent portion 34 and the third bent portion 35 and lets the FPC board 30B bend toward the center of the plane of projection of the imaging element 10B, the projection being made in the optical axis L direction. The first bent portion 33, the second bent portion 34, the third bent portion 35, and the fourth bent portion 36 are bent such that the FPC board 30B is positioned in the plane of projection of the imaging element 10B, the projection being made in the optical axis L direction. A part of the area from the first bent portion 33 to the second bent portion 34 is in contact with the wall 14a.

According to the third embodiment, because the notched portion 14 is provided on the back surface of the imaging element 10B and the part of the area from the first bent portion 33 to the second bent portion 34 is formed in contact with the wall 14a, length of a rigid portion is controlled through prevention of outflow of sealing resin 40 and the bending shapes of the first bent portion 33 and second bent portion 34 are able to be determined easily.

Moreover, a notched portion may be provided further at an opposite position of the back surface of the imaging element 10B, the opposite position being opposite to the position where the bent portion R2 is positioned. FIG. 11 is a diagram schematically illustrating an imaging unit 100C according to a modified example of the third embodiment of the disclosure. (a) of FIG. 11 and (b) of FIG. 11 are a perspective view and a sectional view taken on a vertical plane including an optical axis, of the imaging unit 100C, respectively.

In the imaging unit 100C, a notched portion 14 having a wall 14a forming an inclined surface is formed at a position of a back surface of an imaging element 10C, the position being where a bent portion R2 of an FPC board 30C is positioned, and a notched portion 15 having a wall 15a forming an inclined surface is formed at an opposite position of the back surface of the imaging element 10C, the opposite position being opposite to the position where the bent portion R2 is positioned. The notched portion 14 and the notched portion 15 are formed over the entire width (in a depth direction of the page) of the imaging element 10C.

According to the modified example of the third embodiment, because the notched portion 15 is provided on the back surface of the imaging element 10C, due to increase in the contact area between the imaging element 10C and the FPC board 30C, the connection strength is improved.

Fourth Embodiment

According to a fourth embodiment of the disclosure, a part of a base material portion 37 has been removed at a bent portion R2 of an FPC board 30E. FIG. 12 is a diagram schematically illustrating an imaging unit 100E according to a fourth embodiment of the disclosure, (a) a perspective view, and (b) a sectional view taken on a vertical plane including an optical axis, of an imaging unit 100E.

In the imaging unit 100E, similarly to the second embodiment, a protruding portion 60 is formed at a position of a back surface of an imaging element 10, the position being where the bent portion R2 of the FPC board 30E is positioned.

The FPC board 30E includes the base material portion 37 that is insulating and a wiring portion 38, and the part of the base material portion 37 has been removed at the bent portion R2. A part of the wiring portion 38 is in contact with the protruding portion 60 at a second bent portion 34, the part being where the base material portion 37 has been removed.

According to the fourth embodiment, by the removal of the part of the base material portion 37 at the bent portion R2, thickness of the second bent portion 34 is lessened. As a result, the second bent portion 34 is easily bent or the bending radius R is able to be decreased. Furthermore, because spring-back caused by elasticity of the base material portion 37 is able to be reduced, variation in the bending radius R is able to be reduced.

Figure 13:
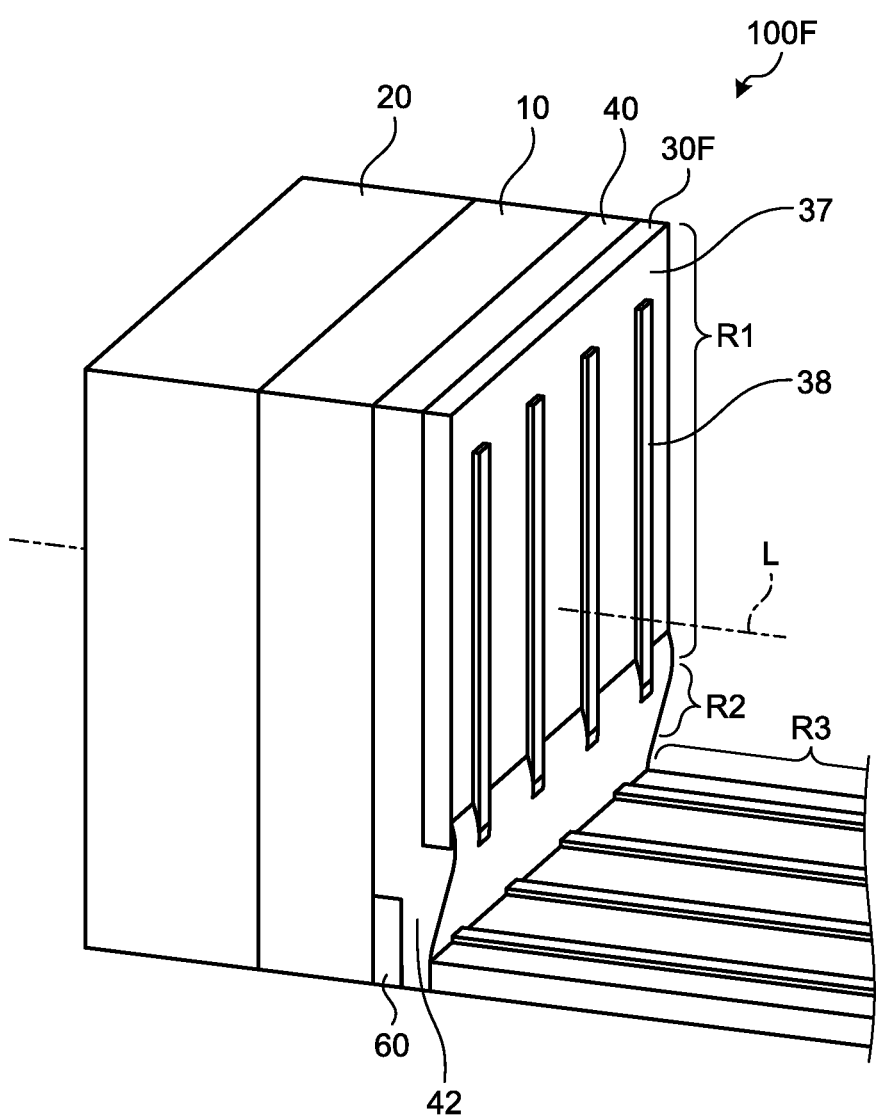
FIG. 13 is a perspective view of an imaging unit according to a first modified example of the fourth embodiment of the disclosure.

According to the above described fourth embodiment, sealing resin 40 is disposed only between the imaging element 10 and the FPC board 30E, but sealing resin 42 may seal around the part of the wiring portion 38, the part being where the base material portion 37 has been removed at the bent portion R2. FIG. 13 is a perspective view of an imaging unit 100F according to a first modified example of the fourth embodiment of the disclosure.

In the imaging unit 100F, sealing resin 42 seals around a part of a wiring portion 38, that is, around a flying lead, the part being where a base material portion 37 has been removed at a bent portion R2. Effects similar to those of the fourth embodiment are thereby able to be achieved and strength of the bent portion R2 is able to be improved.

Figure 14:
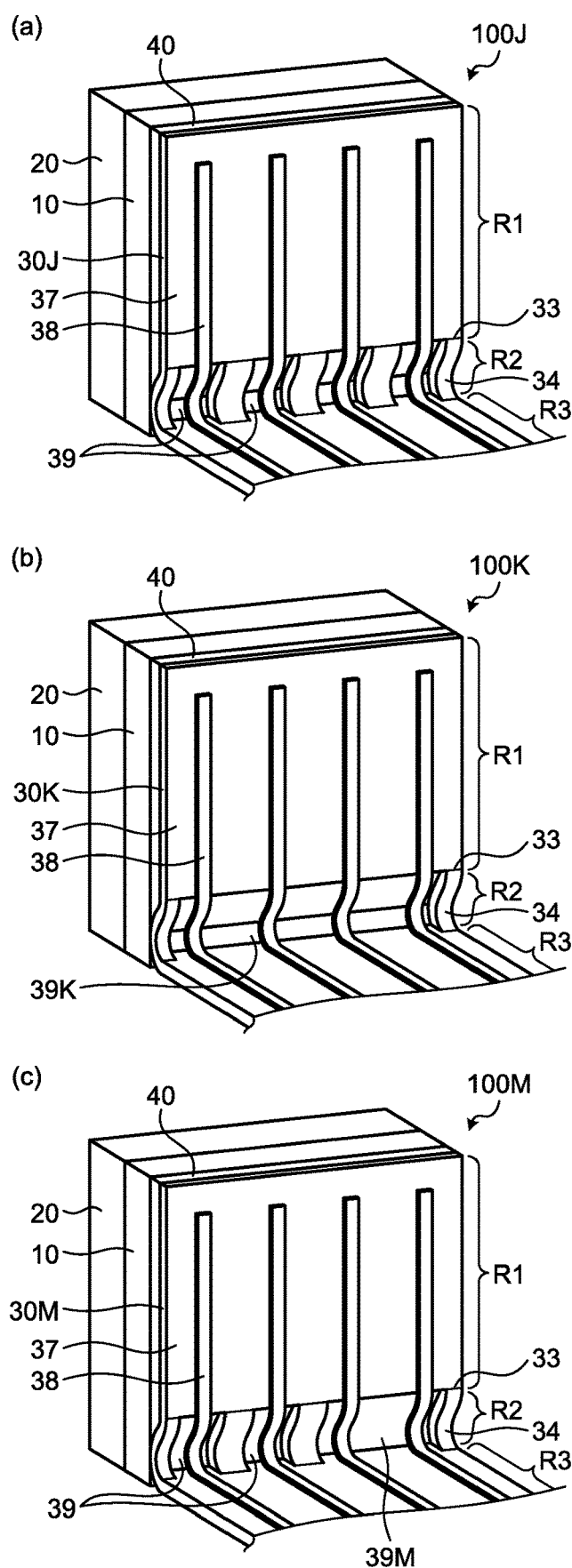
FIG. 14 is perspective views of imaging units according to (a) a second modified example, (b) a third modified example, and (c) a fourth modified example, of the fourth embodiment of the disclosure.

Moreover, according to the fourth embodiment, the part of the base material portion 37 has been removed over the entire width of the bent portion R2, but only a part of the base material portion 37 may be removed, the part being around the wiring portion 38. FIG. 14 is perspective views of imaging units according to (a) a second modified example, (b) a third modified example, and (c) a fourth modified example, of the fourth embodiment of the disclosure.

As illustrated in (a) of FIG. 14, in an imaging unit 100J according to the second modified example, an FPC board 30J has an opening portion 39 formed therein for each wiring portion 38 by removal of a part of a base material portion 37, the part being around each wiring portion 38. In the second modified example, short circuits caused by contact between adjacent wiring portions 38 at a bent portion R2 are able to be prevented.

Moreover, as illustrated in (b) of FIG. 14, in an imaging unit 100K, a bent portion R2 of an FPC board 30K may have a single large opening 39K by removal of a part of a base material portion 37, the part excluding both ends of the base material portion 37.

Moreover, as illustrated in (c) of FIG. 14, in an imaging unit 100M, a bent portion R2 of an FPC board 30M may have openings 39 and 39M having different sizes, according to intervals between wiring portions 38.

In the second to fourth modified examples, similarly to the fourth embodiment, thickness of their second bent portions 34 is reduced, and the second bent portions 34 are thereby able to be easily bent or their bending radii R are able to be reduced, spring-back due to elasticity of their base material portions 37 is thereby able to be reduced, and variation in their bending radii R is thus able to be reduced.

Fifth Embodiment

According to a fifth embodiment of the disclosure, a first bent portion 33 and a second bent portion 34 of a bent portion R2 are disposed at a center portion of a back surface of an imaging element 10G and a bending angle θ of the second bent portion 34 is an obtuse angle. FIG. 15 is a diagram schematically illustrating an imaging unit 100G according to a fifth embodiment of the disclosure. (a) of FIG. 15 and (b) of FIG. 15 are a perspective view and a sectional view taken on a vertical plane including an optical axis, of an imaging unit 100G, respectively.

A connection terminal 12 of the imaging element 10G is formed only at one side (upward on the page) of the back surface of the imaging element 10G and is connected to a connection electrode 32 formed in a connection electrode forming region R1 of an FPC board 30G via a bump 13.

A bent portion R2 of the FPC board 30G is formed of: the first bent portion 33 that is bent toward the imaging element 10G from the connection electrode forming region R1; the second bent portion 34 that lets a cable connection electrode forming region R3 extend in a direction opposite to a direction toward the imaging element 10G; and a fifth bent portion 45 that is bent such that the cable connection electrode forming region R3 is positioned in a plane of projection of the imaging element 10G, the projection being made in an optical axis L direction of the imaging element 10G. The first bent portion 33, the second bent portion 34, and the fifth bent portion 45 are bent, such that the FPC board 30G is positioned in the plane of projection of the imaging element 10G, the projection being made in the optical axis L direction. The second bent portion 34 is bent to form the obtuse angle θ.

According to the fifth embodiment, because the bending angle θ of the second bent portion 34 having the smallest bending angle is an obtuse angle, the bending load of the FPC board 30G is able to be reduced.

Sixth Embodiment

Figure 16:
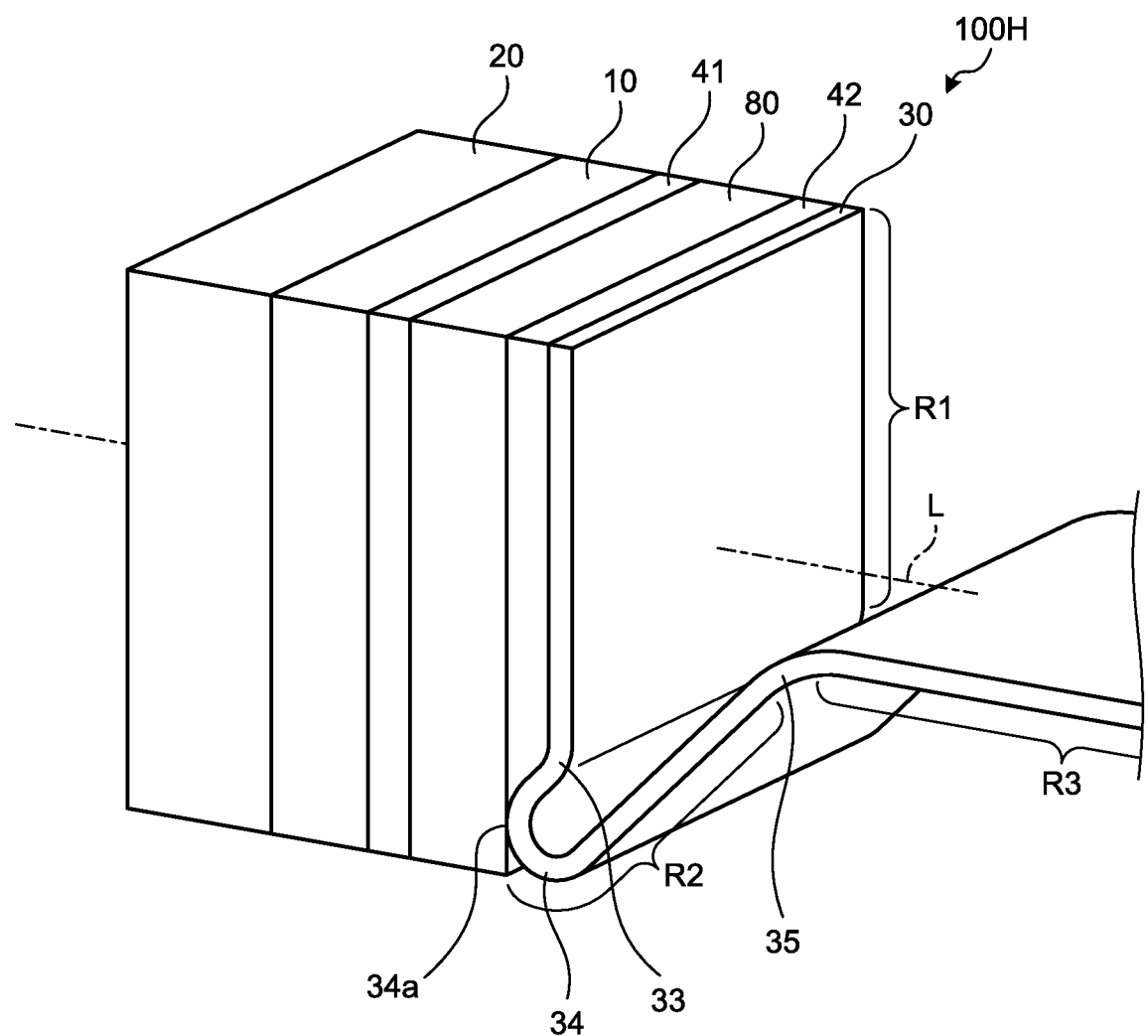
FIG. 16 is a perspective view of an imaging unit according to a sixth embodiment of the disclosure.

According to a sixth embodiment of the disclosure, a silicon substrate 80 having a planar electronic device formed thereon is mounted. FIG. 16 is a perspective view of an imaging unit 100H according to the sixth embodiment of the disclosure.

In the imaging unit 100H, the silicon substrate 80 having the planar electronic device formed thereon is connected on a back surface side of an imaging element 10 and an FPC board 30 is connected to a back surface of the silicon substrate 80. According to this specification, the silicon substrate 80 is also included in the back surface of the imaging element 10.

Sealing resin 41 is filled to a junction between the imaging element 10 and the silicon substrate 80, and sealing resin 42 is filled to a junction between the silicon substrate 80 and the FPC board 30.

A bent portion R2 of the FPC board 30 is formed of a first bent portion 33, a second bent portion 34, and a third bent portion 35, and is in contact with the back surface of the silicon substrate 80 at an end portion 34a of the second bent portion 34. The silicon substrate 80 may instead be a ceramic substrate, a three-dimensional substrate made of a molded interconnect device (MID), or a general rigid substrate, needless to say.

According to the sixth embodiment, the first bent portion 33 is bent toward the imaging element 10 and the end portion 34a of the second bent portion 34 is in contact with the silicon substrate 80, and the sealing resin 42 filled around the junction between the silicon substrate 80 and the FPC board 30 is thereby blocked at the contacting portion and thus prevented from flowing outside the end portion 34a (downward on the page). As a result, the sealing resin 42 is able to be prevented from creeping up the bent portion R2 and length of a rigid portion of the imaging unit 100H is able to be controlled.

The disclosure has an effect of enabling length of a rigid portion of an imaging unit to be shortened further.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit, comprising:
   an imaging element including:
      an image sensor configured to receive light and generate an image signal by photoelectrically converting the light; and
      a connection terminal formed on a back surface of the imaging element;
   a flexible printed circuit board including:
      a connection electrode forming region where a connection electrode connected to the connection terminal is formed;
      a cable connection electrode forming region where a cable connection electrode connected to a cable is formed; and
      a bent portion provided between the connection electrode forming region and the cable connection electrode forming region; and
   sealing resin filled around a junction between the imaging element and the flexible printed circuit board, wherein the bent portion includes:
      a first bent portion that is bent toward the imaging element from the connection electrode forming region located parallelly to the image sensor of the imaging element; and
      a second bent portion that is provided continuously with the first bent portion and lets the cable connection electrode forming region extend in a direction opposite to a direction toward the imaging element, and
   a part of the second bent portion is in contact with the back surface of the imaging element.

2. The imaging unit according to claim 1, wherein a protruding portion is formed at a position of the back surface of the imaging element, the position being where the bent portion is positioned, and a part of the second bent portion is in contact with the protruding portion.

3. The imaging unit according to claim 1, wherein the bent portion includes a third bent portion, and bending of the bent portion at the third bent portion lets the cable connection electrode forming region be disposed to be positioned near a center of a plane of projection of the imaging element, the projection being made in an optical axis direction of the imaging element.

4. The imaging unit according to claim 1, wherein the flexible printed circuit board includes:
   a base material portion that is insulating; and
   a wiring portion, and
   a part of the base material portion has been removed at the bent portion.

5. The imaging unit according to claim 4, wherein sealing resin covers around a part of the wiring portion, the part being where the base material portion has been removed.

6. The imaging unit according to claim 1, further comprising:
   a substrate on a back surface of the imaging element, the substrate being selected from a group including:
      a silicon substrate;
      a ceramic substrate;
      a three-dimensional substrate made of a molded interconnect device; and
      a rigid substrate, wherein
   a front surface of the substrate is connected to the back surface of the imaging element, the flexible printed circuit board is connected to a back surface of the substrate, and the second bent portion is in contact with the back surface of the substrate.

7. The imaging unit according to claim 1, wherein a notched portion having a wall forming an inclined surface is formed at a position of the back surface of the imaging element, the position being where the bent portion is positioned, and a part of an area from the first bent portion to the second bent portion is in contact with the wall.

8. The imaging unit according to claim 7, wherein a notched portion having a wall forming an inclined surface is formed at an opposite position of the back surface of the imaging element, the opposite position being opposite to the position where the bent portion is positioned.

9. The imaging unit according to claim 1, wherein the flexible printed circuit board is positioned in a plane of projection of the imaging element, the projection being made in an optical axis direction of the imaging element.

10. An endoscope, comprising:
    the imaging unit according to claim 1; and
    an insertion portion that has a distal end portion and is insertable into a subject, the distal end portion being formed of a rigid member and being tubular, wherein
    the insertion portion includes the imaging unit in a space inside the distal end portion.

* * * * *